United States Patent
Walker et al.

(10) Patent No.: US 6,287,575 B1
(45) Date of Patent: *Sep. 11, 2001

(54) VACCINE AGAINST PAPILLOMATOUS DIGITAL DERMATITIS (PDD)

(75) Inventors: Richard L. Walker, Davis; Deryck H. Read, Yucaipa; David W. Hird, Davis; Rance B. Lefebvre, Davis; Steven L. Berry, Davis; James S. Cullor, Woodland, all of CA (US); Hank M. Lefler, Reno, NV (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/943,571

(22) Filed: Oct. 3, 1997

(51) Int. Cl.⁷ .............................. C12N 1/00; A61K 39/02; A61K 39/00; A01N 63/00

(52) U.S. Cl. .................................... 424/262.1; 424/234.1; 424/184.1; 424/93.1; 424/93.4; 424/823; 435/243; 435/252.1

(58) Field of Search .............................. 424/184.1, 234.1, 424/262.1, 93.1, 93.4, 823; 435/243, 252.1

(56) References Cited

U.S. PATENT DOCUMENTS

| | | | |
|---|---|---|---|
| 4,919,929 | * | 4/1990 | Beck ........................................ 424/88 |
| 5,266,313 | * | 11/1993 | Esposito et al. ........................ 424/89 |
| 5,492,694 | * | 2/1996 | Nagaraja et al. ................... 424/236.1 |
| 6,096,323 | * | 8/2000 | Walker et al. ..................... 424/262.1 |

FOREIGN PATENT DOCUMENTS

98/05755 * 2/1998 (WO) .............................. C12N/1/00

OTHER PUBLICATIONS

Barber, DM, Veterinary Record, vol. 105(9), pp. 194–195, Sep. 1, 1979.*
Brook, I et al, Journal of Infectious Diseases, Jun. 1984, vol. 149(6), pp. 924–928*
Egerton, JR, Australian Veterinary Journal, Mar. 1970, vol. 46(3), pp. 114–115.*
Egerton, JR, Australian Veterinary Journal, Feb. 1974, vol. 50(2), pp. 59–62.*
Egerton, JR et al, Australian Veterinary Journal, Nov. 1970, vol. 46(11), pp. 517–522.*
Egerton, JR et al, Australian Veterinary Journal, Mar. 1973, vol. 49(3), pp. 139–145*
Egerton, JR et al, Veterinary Record, Nov. 4, 1972, vol. 91–(19), pp. 447–453*
Egerton, JR et al, Veterinary Record, Feb. 3, 1979, vol. 104(5), pp. 98–100.*
Kerry, JB et al, Veterinary Record, May 29, 1976, vol. 98(22), pp. 446–447.*
Peterse, DJ, Veterinary clinics of North America, vol. 1(1), Mar. 1985, pp. 83–91(abstract only).*
Priz, Duran S et al, British Veterinary Journal, Nov.–Dec. 1990, vol. 146(6), pp. 551–556(abstract only).*
Roberts, DS et al, Veterinary Record, Oct. 28, 1972, vol. 91(18), pp. 428–429.*
Bassett et al. Vet. Rec. 126:164–165, 1990.*
Genbank Accession No. L78125, "Phylogenetic analysis of spirochetes associated with papillomatous digital dermatis"; Deposited in Gene Sequence Database at National Center for Genomic Research, May 23, 1996.
Genbank Accession No. L78126, "Phylogenetic analysis of spirochetes associated with papillomatous digital dermatitis"; Deposited in Gene Sequence Database at National Center for Genomic Research, May 23, 1996.
Collighan, et al., "Spriochaetes and other bacterial species associated with bovine digital dermatitis"; *Fems Microbiology Letters*, vol. 156, p 37–41 (Nov., 1997).
Demirkan, et al., "Serological Evidence of Spirochaetal Infections Associated with Digital Dermatitis in Dairy Cattle"; *The Veterinary Journal*, vol. 157, p 69–77, (Jan., 1999).
Murray, et al., *Bergey's Manual of Systematic Bacteriology*, vol. 1, p. 49–57, (1984), Williams & Wilkins.
Hygieia Biological Laboratories, (1996) "Papillomatous Digital Dermatitis Treatment using *Serpens ssp.* bacterin" (Product information).
Addie, D.D., et al. "Control of feline coronavirus infection in kittens", *Veterinary Record* 126:164–165.
Blowey, R.W., et al. (1988) "Digital dermatitis in dairy cattle", *Veterinary Record* 122:505–508.
Blowey, R.W., et al. (1994) "Observations on the pathogenesis of digital dermatitis in cattle" *Veterinary Record*, 135:115–117.
choi, B.–K., et al. (1997) "Spirochetes from Digital Dermatitis Lesions in Cattle Are Closely Related to Treponemes Associated with Human Periodontitis", *International Journal of Systematic Bacteriology* 47(1):175–181.
Döpfer, D., et al. (1997) "Histological and bacteriological evaluation of digital dermatitis in cattle, with special reference to spirochaetes and *Campylobacter faecalis*", *Veterinary Record*, 140:620–623.
Read, D.H., et al. (1992) "An invasive spirochaete associated with interdigital papillomatosis of dairy cattle", *Veterinary Record* 130:59–60.

(List continued on next page.)

Primary Examiner—Lynette R. F. Smith
Assistant Examiner—Ginny Allen Portner
(74) Attorney, Agent, or Firm—Townsend and Townsend and Crew LLP

(57) ABSTRACT

This invention relates to the diagnosis and prevention of ungulate diseases caused by the spirochete bacteria Treponema. The invention specifically relates to isolated cultures of this spirochete and isolated nucleic acids and proteins.

7 Claims, No Drawings

OTHER PUBLICATIONS

Read, D.H., et al. (1995) "Studies on the Etiology of Papillomatous Digital Dermatitis (Footwarts) of Dairy cattle", 38th Annual Meeting —American Association of Veterinary Laboratory Diagnosticians (Abstracts) 68.

Read, D.H., et al. (1996) "Experimental transmission of Papillomatous Digital Dermatitis (Footwarts) in Cattle" (Abstract), *Bet. Pathol* 33:(5)P607 (No. 151).

Rebhun, WIlliam C., et al. (1980) "Interdigital Papillomatosis in Dairy Cattle", JAVMA 177(5):437–440.

Rijpkema, S.G.T., et al. (1997) "Partial identification of spirochaetes from two dairy cows with digital dermatitis by polymerase chain reaction analysis of the 16S robosomal RNA gene", *Veterinary Record* 140:257–259.

Scavia, g., et al. (1994) "Digital Dermatitis: Further contributions on clinical and pathological aspects in some herds in northern Italy", Eighth Internaional Symposium on Disorders of the Ruminant Digit and International Conference on Bovine Lameness (Proceedings and Abstracts), 174–175.

Zemljic, Borut (1994) "Current Investigations into the Causeof Dermatitis Digitalis in cattle", Eighth International Symposium on Disorders of the Ruminant Digit and International Conference on Bovine Lameness (Proceedings and Abstracts), 164–167.

Walker, R.L., et al. (1996) "Humoral Response of Dairy Cattle to Spirochetes Associated with Papillomatous Digital Dermatitis", The Conference of Research Workers in Animal Diseases—Abstracts, No. 36.

Walker, R.L., et al. (1995) "Spirochetes isolated from dairy cattle with papillomatous digital dermatitis and interdigital dermatitis", *veterinary microbiology* 47:343–355.

Walker, R.L., et al. (1997) "Humoral response of dairy cattler to spirochetes isolated from papillomatous digital dermatitis lesions", AJVR 58(7):744–748.

Walker, PD et al, Developments in biological Standardization, vol. 65, pp. 227–236, 1986 (abstract only).*

* cited by examiner

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1503 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: rRNA
      (B) LOCATION: 1..1503
      (D) OTHER INFORMATION: /product= "16S rRNA"
          /note= "bovine Treponema spirochete strain 2-1498"

(xi) SEQUENCE DESCRIPTION: SEQ ID NO:1:

```
TAGAGTTTGA TCCTGGCTCA GAACGAACGC TGGCGGCGCG TCTTAAGCAT GCAAGTCGAA     60

CGGCAAGGGA GGAGCTTGCT TCTCCCCTAG AGTGGCGGAC TGGTGAGTAA CGCGTGGGTG    120

ATCTGCCCTT AAGATGGGGA TAGCTCCTAG AAATAGGAGG TAATACCGAA TACGCTTATA    180

CGGATAAAGC CGTATAAGGA AAGGAGCCTA CGACCTTGCT TGAGGATGAG CCCGCGTCCA    240

TTAGCATGTT GGTGAGGTAA CGGCTTACCA AGGCGACGAT GGGTATCCGG CCTGAGACAG    300

GATCAAACTC TATTGGGACT GAGATACGGC CCAAACTCCT ACGGGAGGCA GCAGCTAAGA    360

ATATTCCGCA ATGGACGGAA GTCTGACGGA GCGACGCCGC GTGGACGAAG AAGGCCGAAA    420

GGTTGTAAAG TTCTTTTGCC GATGAAGAAT AAGAGGATGA GGGAATGCGT CCTTGATGAC    480

GGTAGTCGAG CGAATAAGCC CCGGCTAATT ACGTGCCAGC AGCCGCGGTA ACACGTAAGG    540

GGCGAGCGTT GTTCGGAATT ATTGGGCGTA AAGGGCACGC AGGCGGGTTG GTAAGCCTGA    600

TGTGAAATAC TCAAGCTTAA CTTGAGAATT GCATTGGGTA CTGCCAGTCT TGAATCACGG    660
```

```
AGGGGAAACC GGAATTCCAA GTGTAGGGGT GGAATCTGTA GATATTTGGA AGAACACCGG      720

TGGCGAAGGC GGGTTTCTGG CCGATGATTG ACGCTGAGGT GCGAAGGTGT GGGGAGCAAA      780

CAGGATTAGA TACCCTGGTA GTCCACACAG TAAACGATGT ACACTAGGTG TTGGGGCAAG      840

AGCTTCAGTG CCGGCGCAAA CGCAATAAGT GTACCGCCTG GGGAGTATGC CCGCAAGGGT      900

GAAACTCAAA GGAATTGACG GGGCCCGCA CAAGCGGTGG AGCATGTGGT TTAATTCGAT       960

GATACGCGAG GAATCTTACC TGGGTTTGAC ATCAAAAGCA ATATTATAGA GATATGGTAG     1020

CGTAGCAATA CGGCTTTTGA CAGGTGCTGC ATGGCTGTCG TCAGCTCGTG CCGTGAGGTG     1080

TTGGGTTAAG TCCCGCAACG AGCGCAACCC CTACTGTCAG TTGCTAACAG GTAATGCTGA     1140

GGACTCTGGC GGAACTGCCG ATGACAAATC GGAGGAAGGT GGGGATGACG TCAAGTCATC     1200

ATGGCCCTTA TGTCCAGGGC TACACACATG TTACAATGGT TGCTACAAAA TGAAGCGAGA     1260

CTGTGAGGTT AAGCAAATCG CAAAAAAGCA ATCGTAGTTC GGATTGAAGT CTGAAACTCG     1320

ACTTCATGAA GTTGGAATCG CTAGTAATCG CACATCAGCA CGGTGCGGTG AATACGTTCC     1380

CGGGCCTTGT ACACACCGCC CGTCACACCA TCCGAGTTGA GGGTACCCGA AGTCGCCAGT     1440

CTAACCCTAA GGGAGAGCGG TGCCGAAGGT ATGTTTTGGC AAGGAAGGTT GAAGTCGTAA     1500

CAA                                                                    1503

(2) INFORMATION FOR SEQ ID NO:2:

(i) SEQUENCE CHARACTERISTICS:
        (A) LENGTH: 1490 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: rRNA
        (B) LOCATION: 1..1490
        (D) OTHER INFORMATION: /product= "16S rRNA"
            /note= "bovine Treponema spirochete
            strain 1-9185MED"

(xi) SEQUENCE DESCRIPTION: SEQ ID NO:2:

TAGAGTTTGA TCCTGGCTCA GAACGAACGC TGGCGGCGCT TCTTAAGCAT GCAAGTCGAA       60

CGGCAAGGGA GGAGCTTGCT CTCCCCTAGA GTGGCGGACT GGTGAGTAAC GCGTGGGTGA      120

TCTGCCCTTA AGATGGGGAT AGCTCCTAGA AATAGGAGGT AATACCGAAT GCGCTTATAC      180

GGATAAAGCC GTATAAGGAA AGGAGCTACG GCTCCGCTTT AGGATGGGCC TGCGTCCCAT      240

TAGCTTGTTG GTGAGGTAAC GGCCCACCAA GGCGACGATG GGTATCCGGC CTGAGAGGGT      300

GAACGGACAC ATTGGGACTG AGATACGGCC CAAACTCCTA CGGGAGGCAG CAGCTAAGAA      360

TCTTCCGCAA TGGACGAAAG TCTGACGGAG CGACGCCGCG TGAATGAAGA AGGCTGAAAA      420

GTTGTAAAAT TCTTTTGCAG ATGAAGAATA AGGAGATGAG GGAATGCTTC TTCGATGACG      480

GTAGTCATGC GAATAAGGGG CGGCTAATTA CGTGCCAGCA GCCGCGGTAA CACGTAAGCC      540

CCAAGCGTTG TTCGGAATTA TTGGGCGTAA AGGGCATGTA GGCGGTTATG TAAGCCTGAT      600

GTGAAATCTA CGAGCTTAAC TCGTAAACTG CATTGGGTAC TGCGTAACTT GAATCACGGA      660

GGGGAAACCG GAATTCCAAG TGTAGGGGTG GAATCTGTAG ATATTTGGAA GAACACCGGT      720

GGCGAAGGCG GGTTTCTGGC CGATGATTGA CGCTGAGATG CGAAGGTGCG GGAGCAAAC      780

AGGATTAGAT ACCCTGGTAG TCCGCACAGT AAACAATGTA CACTAGGCGT TGGAGCAAGA      840
```

```
GCTTCAGTGC CGACGCAAAC GCATTAAGTG TACCGCCTGG GAAGTATGCC CGCAAGGGTG      900

AAACTCAAAG GAATTGACGG GGGCCACACA AGCGGTGGAG CATGTGGTTT AATTCGATGA      960

TACGCGAGGA ACCTTACCTG GGTTTGACAT CAAGAGTAAT GGTATAGAGA TATATCAGCG     1020

TAGCAATACG ACTCTTGACA GGTGCTGCAT GGCTGTCGTC AGCTCGTGCC GTGAGGTGTT     1080

GGGTTAAGTC CCGCAACGAG CGCAACCCCT ACTGCCAGTT ACTAACACGT AAAGGTTGAG     1140

GACTCTGGCG GAACTGCCGA TGACAAATCG GAGGAAGGTG GGGATGACGT CAAGTCATCA     1200

TGGCCCTTAC GTCCAGGGCT ACACACGTGC TACAATGGTT GCTACAAATC GAAGCGACGC     1260

CGCGAGGCCA AGCAAAACGC AAAAAAGCAA TCGTAGTCCG GATTGAAGTC TGAAACTCGA     1320

CTTCATGAAG TTGGAATCGC TAGTAATCGC ACATCAGCAC GGTGCGGTGA ATACGTTCCT     1380

GGGCCTTGTA CACACCGCCC GTCACACCAT CCGAGTCGAG GGTACCGGAA GCCGCTAGTC     1440

TAGCCCGCCC GGGAGGACGG TGTCCAAGGT TCGCTTGGTA AGGAGGGTGA              1490
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "forward primer"

(xi) SEQUENCE DESCRIPTION: SEQ ID NO:3:

```
AGAGTTTGAT CCTGGCTCAG                                                   20
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "reverse primer"

(xi) SEQUENCE DESCRIPTION: SEQ ID NO:4:

```
GGTTACCTTG TTACGACTT                                                    19
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..17
        (D) OTHER INFORMATION: /note= "forward primer"

(xi) SEQUENCE DESCRIPTION: SEQ ID NO:5:

```
TGCTTGAGGA TGAGCCC                                                              17

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "reverse primer"

(xi) SEQUENCE DESCRIPTION: SEQ ID NO:6:

AAGCAAGGTC GTAGGCTCC                                                            19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "forward primer"

(xi) SEQUENCE DESCRIPTION: SEQ ID NO:7:

AAGAATAAGG AGATGAGGG                                                            19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..19
        (D) OTHER INFORMATION: /note= "forward primer"

(xi) SEQUENCE DESCRIPTION: SEQ ID NO:8:

ATGAGGGAAT GCGTCCTTG                                                            19

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "forward primer"
```

(xi) SEQUENCE DESCRIPTION: SEQ ID NO:9:

AAGGGTGAAA CTCAAAGG                                                    18

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "forward primer"

(xi) SEQUENCE DESCRIPTION: SEQ ID NO:10:

CAGGATCAAA CTCTATTGGG                                                  20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "reverse primer"

(xi) SEQUENCE DESCRIPTION: SEQ ID NO:11:

TTCACCCTTG CGGGCATACT                                                  20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "forward primer"

(xi) SEQUENCE DESCRIPTION: SEQ ID NO:12:

ATTACGTGCC AGCAGCCGCG                                                  20

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..15
        (D) OTHER INFORMATION: /note= "reverse primer"

(xi) SEQUENCE DESCRIPTION: SEQ ID NO:13:

CTGCTGCCTC CCGTA                                                                15

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "reverse primer"

(xi) SEQUENCE DESCRIPTION: SEQ ID NO:14:

CGTATTACCG CGGCTGCT                                                             18

VACCINE AGAINST PAPILLOMATOUS DIGITAL DERMATITIS (PDD)

FEDERALLY SPONSORED RESEARCH OR DEVELOPMENT

This invention was made with Government support under Grant No. CALV AH 144, awarded by the United States Department of Agriculture. The Government has certain rights in this invention.

CROSS REFERENCE TO RELATED APPLICATIONS

Not applicable.

FIELD OF THE INVENTION

This invention relates to the diagnosis and prevention of ungulate diseases caused by treponeme spirochete bacteria. The invention specifically relates to isolated cultures of these spirochetes and their isolated nucleic acids and proteins.

BACKGROUND OF THE INVENTION

Over the past few years, there has been a marked increase in the prevalence of related painful diseases of the feet of dairy cattle called papillomatous digital dermatitis (PDD), digital dermatitis (DD) or interdigital dermatitis (IDD), hereinafter referred to as PDD. Commonly known as footwarts, PDD has been reported in the USA, Canada, Europe, the Mediterranean, Japan, South Africa, Australia, and South America. This disease adversely affects the dairy industry economically through increased treatment costs and by its negative effect on milk production and reproductive performance. It appears as a contagious disease, with some herds having a 90% prevalence of clinical disease.

PDD causes severe lameness, decrease in body condition, and decreased reproductive performance in cattle. First calf heifers are most often affected. Little or no digital swelling occurs. The lesions are limited to the feet, usually the hind feet. Typically, lesions occur at the back of foot near the interditigal ridge. Lesions may range from small, dime-sized, flat, red and circumscribed lesions (early lesions) to large, raised, golf-ball sized, with long brown/black papillary fronds (mature lesions). The long (true) hairs at edge of lesion are frequently hypertrophied. The lesions may persist for many months or may regress in dry weather.

Various attempts to demonstrate viruses, structural group antigens of papillomavirus, and bovine papillomavirus types 1–6 in PDD have been negative (Basset et al., Vet. Rec. 126:164–165 (1990); Read et al., Vet. Rec. 130:59–60 (1992); Read et al., Proc. Amer. Ass. Vet. Lab. Diag. 38:68 (1995); Rebhun, et al., J. Am. Vet. Med. Assoc. 177:437–440 (1980); Scavia et al., Proc. Int. Sym. Dis. Rum. Digit 8:174–176 (1994); Zemljic, Proc. Int. Sym. Rum. Digit 8:164–167 (1994)). Histologic examination for Dermatophilus spp., fungi, and parasites also have been negative (Read et al., Proc. Amer. Ass. Vet. Lab. Diag. 38:68 (1995)).

Because the disease responds to topical or parenteral treatment with antibiotics, a bacterial role in the disease process has been indicated. Spirochetes have been demonstrated invading into the stratum spinosum and dermal papillae of PDD lesions and are the predominant bacterial morphotype present. Spirochetes with morphologic, phenotypic, and genetic characteristics of the genus Treponema have been isolated from PDD lesions (Walker et al., Vet. Micro. 47:343–355 (1995); Walker et al., AJVR 58:744–748 (1997)). Intralesional invasive spirochetes have also been demonstrated in PDD worldwide (Blowey et al., Vet. Rec. 135, 115–117 (1994); Scavia et al., Proc. Int. Sym. Dis. Rum. Digit 8:174–176 (1994); Zemljic, Proc. Int. Sym. Rum. Digit 8:164–167 (1994); Kimura et al., J. Vet. Med. Jpn. 46:899–906 (1993); Dopfer et al., Vet. Rec. 140:620–623 (1997); Choi et al., Int. J. Syst. Bact. 47:175–181 (1997); Rijpkema et al., Vet. Rec. 140:257–259 (1997)).

It remains unclear whether these spirochete organisms have a primary role in lesion development or whether they act as secondary opportunists after the initial PDD lesion has developed. For example, other bacteria such as Serpens spp., a gram negative rod related to members of the genus Pseudomonas, have also been suggested as a PDD agent. In the field, PDD appears contagious but most previous attempts to transmit PDD experimentally have not been successful (Weaver, Proc. 7th Biann. Int. Sym. Dis. Rum. Digit, Copenhagen (1992); Basset et al., Vet. Rec. 126:164–165 (1990); but see Read & Walker, Vet. Pathology 33:607 (1996)).

Currently, the etiologic agent of PDD is unknown. In addition, it is unknown whether PDD can spread to other species, although similar histopathologic lesions have been observed in sheep, horses, and goats. There is therefore a need to definitively identify the etiologic agent for PDD and to develop a means of preventing this disease by developing a vaccine against PDD.

SUMMARY OF THE INVENTION

The present invention identifies ungulate Treponema spp. as the etiologic agents of ungulate papillomatous digital dermatitis (PDD). The invention therefore provides isolated cultures of Treponema spp., vaccines that effectively immunize susceptible ungulates against PDD, and methods of diagnosing PDD by detecting infection with Treponema spp.

In one aspect, the invention provides a biologically pure culture of ungulate Treponema.

In one embodiment, the culture has all the characteristics of Treponema strain 1-9185MED (ATCC Accession No. 202030) or Treponema strain 2-1498 (ATCC Accession No. 202031). In another embodiment, the culture is selected from the group consisting of Treponema strain 1-9185MED (ATCC Accession No. 202030) and Treponema strain 2-1498 (ATCC Accession No. 202031).

In another aspect, the invention provides a pharmaceutical composition comprising a pharmaceutically acceptable carrier and an immunogenically effective amount of an ungulate Treponema antigen.

In another aspect, the invention provides a method for inducing an immune response against ungulate Treponema. This method includes the step of administering to an ungulate animal a pharmaceutical composition comprising a pharmaceutically acceptable carrier and an immunogenically effective amount of an ungulate Treponema antigen.

In one embodiment, the composition further includes an antigen from an organism that causes ungulate foot rot selected from the group consisting of Fusobacterium necrophorum, Porphyromonas levii, and Dichelobacter nodosus. In another embodiment, the pharmaceutical composition further comprises a bovine respiratory syncytial virus antigen, a bovine Herpes virus antigen, a leptospiral antigen, a bovine diarrhea virus antigen, a bovine parainfluenza virus antigen, a vesicular stomatitis virus antigen, a malignant catarrhal fever virus antigen, a blue tongue virus antigen, a pseudorabies virus antigen, a rabies virus antigen, a rinderpest virus antigen, a *Fusobacterium necrophorum* antigen, a *Dichelobacter nodosus* antigen, or a Clostridia spp. antigen.

In another embodiment, the ungulate Treponema antigen is from Treponema strain 1-9185MED (ATCC Accession No. 202030) or Treponema strain 2-1498 (ATCC Accession No. 202031). In another embodiment, the antigen is a biologically pure culture of Treponema. In another embodiment, the antigen is selected from the group consisting of Treponema strain 1-9185MED (ATCC Accession No. 202030) and Treponema strain 2-1498 (ATCC Accession No. 202031). In another embodiment, the ungulate Treponema antigen is an isolated Treponema polypeptide. In another embodiment, the polypeptide is recombinantly produced.

In another embodiment, the pharmaceutical composition is administered parenterally.

In another aspect, the invention provides a method of detecting the presence of antibodies specifically immunoreactive with an ungulate Treponema antigen in a biological sample. This method includes the steps of contacting the sample with the Treponema antigen, thereby forming a antigen/antibody complex; and detecting the presence or absence of the complex.

In one embodiment, the Treponema antigen is from Treponema strain 1-9185MED (ATCC Accession No. 202030) or Treponema strain 2-1498 (ATCC Accession No. 202031). In another embodiment, the biological sample is bovine serum. In another embodiment, the antigen is an isolated Treponema polypeptide. In another embodiment, the antigen is immobilized on a solid surface. In another embodiment, the complex is detected using a labeled anti-bovine antibody.

In another aspect, the invention provides a method of detecting the presence of ungulate Treponema in a biological sample. This method includes the steps of contacting the sample with an antibody specifically immunoreactive with a Treponema antigen, thereby forming a antigen/antibody complex; and detecting the presence or absence of the complex.

In one embodiment, the antibody is specifically immunoreactive with a Treponema strain 1-9185MED (ATCC Accession No. 202030) antigen or a Treponema strain 2-1498 (ATCC Accession No. 202031) antigen. In another embodiment, the antibody is a monoclonal antibody. In another embodiment, the antibody is immobilized on a solid surface. In another embodiment, the complex is detected using a second labeled antibody. In another embodiment, the biological sample is ungulate foot tissue.

In another aspect, the invention provides a method of detecting the presence of ungulate Treponema-specific nucleic acids in a biological sample. This method includes the steps of: contacting the sample with a oligonucleotide probe which specifically hybridizes with a target Treponema-specific polynucleotide sequence, thereby forming a hybridization complex; and detecting the presence or absence of the complex.

In one embodiment, the target Treponema-specific polynucleotide sequence is from Treponema strain 1-9185MED (ATCC Accession No. 202030) or Treponema strain 2-1498 (ATCC Accession No. 202031). In another embodiment, the target Treponema-specific polynucleotide sequence is 16S rRNA. In another embodiment, the target Treponema-specific polynucleotide sequence is SEQ ID NO:1 (16S rRNA from strain 2-1498) or SEQ ID NO:2 (16S rRNA from strain 1-9185MED). In another embodiment, the step of detecting further comprises amplifying the target Treponema-specific polynucleotide sequence.

BRIEF DESCRIPTION OF THE DRAWINGS

Not applicable.

DETAILED DESCRIPTION OF THE INVENTION

I. Introduction

The present invention provides isolated Treponema cultures isolated from cattle. The cultures are useful in a variety of applications, including the production of nucleic acids and proteins for diagnostic assays for PDD and the preparation of immunogenic proteins and compositions for use in PDD vaccine compositions.

II. Definitions

As used herein, the following terms have the meanings ascribed to them unless specified otherwise.

"Biological sample" refers to any sample obtained from a living or dead organism. Examples of biological samples include biological fluids and tissue specimens. Examples of tissue specimens include bovine hoof and foot tissue. Such biological samples can be prepared for analysis using in situ techniques.

A "biologically pure culture" refers to a continuous in vitro culture of ungulate Treponema which is substantially free of other organisms. A culture is substantially free of other organisms if standard harvesting procedures (as described below) result in a preparation which comprises at least about 95%, preferably 99% or more of the organism, e.g., Treponema.

"Ungulate Treponema" and "bovine Treponema" refer to flexible, spiral-shaped spirochete bacteria of the Treponema genus identified in or isolated from ungulate and bovine biological samples, in particular from hoof and foot tissue. "Ungulate" refers to hooved animals such as cows, horses, sheep, and goats. "Bovine" refers to cattle (bulls, cows, calves). Typically, the spirochetes of the Treponema genus can be isolated from foot or hoof tissue of hooved animals infected with PDD. Exemplary Treponema isolates 1-9185MED and 2-1498 isolated from bovine PDD foot tissue have been deposited with the American Type Culture Collection, as described below.

A Treponema "protein" or "polypeptide" includes allelic variations normally found in the natural population and changes introduced by recombinant techniques. Those of skill recognize that proteins can be modified in a variety of ways including the addition, deletion and substitution of amino acids.

Treponema "nucleic acids" and "polynucleotides," as used herein, may be DNA or RNA. One of skill will recognize that for use in the expression of Treponema proteins or as diagnostic probes, polynucleotide sequences need not be identical and may be substantially identical to sequences disclosed here. In particular, where the inserted polynucleotide sequence is transcribed and translated to produce a functional polypeptide, one of skill will recognize that because of codon degeneracy a number of polynucleotide sequences will encode the same polypeptide.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (GAP, BESTFIT, FASTA, and TFASTA in the Wisconsin Genetics Software Package, Genetics Computer Group (GCG), 575 Science Dr., Madison, Wis.), or by inspection.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences are preferably compared to a reference sequence using GAP using default parameters.

Another indication that polynucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at room temperature with a 5×SSC, 0.1% SDS wash.

The phrase "specifically or selectively hybridizing to," refers to hybridization between a probe and a target sequence in which the probe binds substantially only to the target sequence, forming a hybridization complex, when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, $F_{ab}$, and $F(ab)_2$, as well as in single chains. Single-chain antibodies, in which genes for a heavy chain and a light chain are combined into a single coding sequence, may also be used.

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a Treponema peptide or protein, means a chemical composition which is free of other subcellular components of the Treponema organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes high resolution will be needed and HPLC or a similar means for purification utilized.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe. "Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

"Pharmaceutically acceptable" means a material that is not biologically or otherwise undesirable, i.e., the material can be administered to an individual along with a Treponema antigen without causing any undesirable biological effects or interacting in a deleterious manner with any of the other components of the pharmaceutical composition.

III. Isolation and Characterization of Ungulate Treponema from PDD Infected Cows Treponema cultures of the invention have been deposited with the American Type Culture Collection, 10801 University Blvd., Manassas, Va. 20110-2209 on Sep. 16, 1997 and assigned Accession Numbers 202030 (1-9185MED) and 202031 (2-1498).

Treponema isolates that cause PDD are typically obtained from bovine foot tissue of cows infected with PDD (see, e.g., Walker et al., *Vet. Micro.* 47:343–355 (1995)). These cultures are generally inoculated with tissue from foot biopsies or scraping of PDD lesions in affected cow foot tissue. Isolates are grown in suitable bacterial media, preferably oral treponome isolation (OTI) broth or agar. Pure isolates are obtained by plating out cultures, picking individual colonies, propagating the colonies and re-plating to assess purity.

Generally, morphological, histopathological, and immunological characteristics are used to identify isolated Treponema spirochetes causing lesions in the foot tissue of these cows with PDD. Stereomicroscope studies are used to characterize the morphological features of isolates. Distinguishing histopathological and morphological features include active flexing, rotational motility, number of axial filaments, cell diameter, cell length, and wavelength. Enzyme activity of typical enzymes such as alkaline phosphatase, esterase, esterase lipase, acid phosphatase, naphthol-AS-BI-phosphohydrolase, β-galactosidase, β-glucuronidase, and N-acetyl-β-glucosaminidase are evaluated, typically using a commercially available system (e.g., API ZYM, Bio Merieux, France. Restriction enzyme analysis on genomic DNA is performed according to standard methodology. Standard immunoblot analysis is used to examine proteins and other antigens. Antigenically, antigens from isolates generally fell into two groups, those that reacted strongly with 1-9185MED antisera, and those that reacted with 2-1498 antisera. A monoclonal antibody to a *Borrelia burgdorferi* antigen is used as a negative control (another spirochete genus). Based on morphological, histopathological, and antigenic characteristics, Treponema spirochetes can be distinguished from the other seven genera of spirochetes, Borellia, Brachyspira, Cristispira, Leptonema, Leptospira, Serpulina, and Spirochaeta (Holt et al., in *Bergy's Manual of Determinative Bacteriology,* (9th ed. 1994)).

In addition, 16S rRNA sequences for two bovine Treponema isolates were obtained and compared using PCR to the 16S rRNA of other bacteria, including other spirochetes. PCR reactions were performed according to standard methods known to those skilled in the art. Alignment of these sequences with published sequences of *Treponema phagedenis, T. pallidum, T. pectinovorum, T. denticola, T. saccharophilum, T. bryantii,* and *Escherichia coli* showed that the bovine Treponema isolates are genotypically unique. The 16S rRNA sequences from Treponema strain 1-9185MED (SEQ ID NO:2) most closely aligns with *T. denticola,* and 2-1498 (SEQ ID NO:1) most closely aligns with *T. phagedenis,* but the sequences do not show 100% homology. The 16s rRNA from bovine Treponema is therefore useful as a diagnostic tool for PDD. To choose suitable PCR primers for use in diagnostic assays, the 16S rRNAs of the above listed bacterial species are aligned with the 16S rRNA of Treponema strains 1-9185MED and 2-1498 (SEQ ID NO:2 and SEQ ID NO:1, respectively). The sequence alignment allows selection of primers that are used to specifically amplify Treponema strains 1-9185MED and 2-1498. The following primers were used to examine and generate the 16S rRNA of strains 1-9185MED and 2-1498 (SEQ ID NO:2 and SEQ ID NO:1, respectively). The letters "R" and "F" designate reverse and forward respectively. All primers begin with the 5' end (For *E. coli* primer sequences and primers 11 and 12, see Eden et al., *Int. J. Systematic Bacteriol.,* pp. 324–325 (1991)).

1. F-(*E. coli* base 8 to 27) AGAGTTTGATCCTGGCTCAG (SEQ ID NO:3)
2. R-(*E. coli* complement bases 1510 to 1492) ggttaccttgttacgactt (SEQ ID NO:4)
3. F-TGCTTGAGGATGAGCCC (SEQ ID NO:5)
4. R-AAGCAAGGTCGTAGGCTCC (SEQ ID NO:6)
5. F-AAGAATAAGGAGATGAGGG (SEQ ID NO:7)
6. F-ATGAGGGAATGCGTCCTTG (SEQ ID NO:8)
7. F-AAGGGTGAAACTCAAAGG (SEQ ID NO:9)
8. F-CAGGATCAAACTCTATTGGG (SEQ ID NO:10)
9. R-TTCACCCTTGCGGGCATACT (SEQ ID NO:11)
10. F-ATTACGTGCCAGCAGCCGCG (SEQ ID NO:12)
11. R-CTGCTGCCTCCCGTA (SEQ ID NO:13)
12. R-CGTATTACCGCGGCTGCT (SEQ ID NO:14)

| ISOLATE | PRIMER |
|---|---|
| 1-9185MED | 5, 7, 11, 4, 12, 9 |
| 2-1498 | 2, 3, 11, 4 |

As explained in detail below, the isolates are useful in a variety of diagnostic assays as well as pharmaceutical compositions for treatment and prevention of PDD.

IV. Preparation of Treponema Polypeptides and Nucleic Acids

Standard protein isolation and purification techniques can be used to isolate proteins from the cultures provided here. Such techniques include standard immunoblot techniques, selective precipitation with such substances as ammonium sulfate, column chromatography, immunopurification methods, and the like (see, e.g., Scopes, *Protein Purification: Principles and Practice* (1982)).

Once proteins have been identified, standard protein purification methods can be used to purify these proteins and produce polyclonal or monoclonal antibodies for use in diagnostic methods described below. Such antigens are useful in enzyme-linked immunoassays (ELISA) and immunoperoxidase assays on in situ fixed tissue for the detection of Treponema-specific antibodies in PDD infected cattle.

Rather than extract the proteins directly from cultured Treponema, nucleic acids derived from the cultures can be used for recombinant expression of the proteins. In these methods, the nucleic acids encoding the proteins of interest are introduced into suitable host cells, followed by induction of the cells to produce large amounts of the protein. The invention relies on routine techniques in the field of recombinant genetics, well known to those of ordinary skill in the art. A basic text disclosing the general methods of use in this invention is Sambrook et al., *Molecular Cloning, A Laboratory Manual,* Cold Spring Harbor Publish., Cold Spring Harbor, N.Y. 2nd ed. (1989).

Nucleic acids for use as diagnostic oligonucleotide probes or for the recombinant expression of proteins can be isolated using a number of techniques. For instance, portions of proteins isolated from the cultures discussed above can be sequenced and used to design degenerate oligonucleotide probes to screen a cDNA library. Amino acid sequencing is performed and oligonucleotide probes are synthesized according to standard techniques as described, for instance, in Sambrook et al., supra. Alternatively, oligonucleotide probes useful for identification of desired genes can also be prepared from conserved regions of related genes in other species.

Alternatively, amplification techniques such as polymerase chain reaction technology (PCR) can be used to amplify nucleic acid sequences of the desired gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of the mRNA in physiological samples, for nucleic acid sequencing, or for other purposes (for a general overview of PCR, see *PCR Protocols: A Guide to Methods and Applications.* (Innis et al., eds., 1990)0.

Standard transfection methods are used to produce prokaryotic, mammalian, yeast or insect cell lines which express large quantities of the desired polypeptide, which is then purified using standard techniques (see, e.g., Colley et al., *J. Biol. Chem.* 264:17619–17622, 1989; *Guide to Protein Purification,* supra).

The nucleotide sequences used to transfect the host cells can be modified to yield Treponema polypeptides with a variety of desired properties. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring protein. In general, modifications of the sequences encoding the polypeptides may be readily accomplished by a variety of well-known techniques, such as site-directed mutagenesis (see Gillman & Smith, *Gene* 8:81–97 (1979); Roberts et al., *Nature* 328:731–734 (1987)). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit a protective immune response can be easily determined using in vitro assays. For instance, the polypeptides can be tested for their ability to induce lymphoproliferation, T cell cytotoxicity, or cytokine production using standard techniques.

The particular procedure used to introduce the genetic material into the host cell for expression of the polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

Any of a number of well known cells and cell lines can be used to express the polypeptides of the invention. For instance, prokaryotic cells such as *E. coli* can be used. Eukaryotic cells include, yeast, Chinese hamster ovary (CHO) cells, COS cells, and insect cells.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses.

The expression vector typically contains a transcription unit or expression cassette that contains all the elements required for the expression of the polypeptide DNA in the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

Following the growth of the recombinant cells and expression of the polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the polypeptide can be accomplished by standard techniques, for example, affinity chromatography, ion exchange chromatography, sizing chromatography, $His_6$ tagging and Ni-agarose chromatography (as described in Dobeli et al., *Mol. and Biochem. Parasit.* 41:259–268 (1990)), or other protein purification techniques to obtain homogeneity. The purified proteins are then used to produce pharmaceutical compositions, as described below.

An alternative method of preparing recombinant polypeptides useful as vaccines involves the use of recombinant viruses (e.g., vaccinia). Vaccinia virus is grown in suitable cultured mammalian cells such as the HeLa S3 spinner cells, as described by Mackett et al., in *DNA cloning Vol. II: A practical approach,* pp. 191–211 (Glover, ed.).

V. Antibody Production

The isolated proteins or cultures of the present invention can be used to produce antibodies specifically reactive with Treponema antigens. If isolated proteins are used, they may be recombinantly produced or isolated from Treponema cultures. Synthetic peptides made using the protein sequences may also be used.

Methods of production of polyclonal antibodies are known to those of skill in the art. In brief, an immunogen, preferably a purified protein, is mixed with an adjuvant and animals are immunized. When appropriately high titers of antibody to the immunogen are obtained, blood is collected from the animal and antisera is prepared. Further fractionation of the antisera to enrich for antibodies reactive to Treponema proteins can be done if desired (see Harlow & Lane, *Antibodies: A Laboratory Manual* (1988)).

Polyclonal antisera to the 1-9185MED and 2-1498 isolates have been produced and evaluated. The polyclonal antisera are used to identify and characterize Treponema in the tissues of infected animals using, for instance, in situ techniques and immunoperoxidase test procedures described in Anderson et al. *JAVMA* 198:241 (1991) and Barr et al. *Vet. Pathol.* 28:110–116 (1991) (see also Example 3).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Monoclonal antibodies produced in such a manner are used, for instance, in ELISA diagnostic tests, immunoperoxidase tests, immunohistochemical tests, for the in vitro evaluation of spirochete invasion, to select candidate antigens for vaccine development, protein isolation, and for screening genomic and cDNA libraries to select appropriate gene sequences.

VI. Diagnosis of Treponema Infections

The present invention also provides methods for detecting the presence or absence of Treponema in a biological sample. For instance, antibodies specifically reactive with Treponema can be detected using either Treponema proteins or the isolates described here. The proteins and isolates can also be used to raise specific antibodies (either monoclonal or polyclonal) to detect the antigen in a sample. In addition, the nucleic acids disclosed and claimed here can be used to detect Treponema-specific sequences using standard hybridization techniques. Each of these assays is described below.

A. Immunoassays

For a review of immunological and immunoassay procedures in general, see *Basic and Clinical Immunology* (Stites & Terr ed., 7th ed. 1991)). The immunoassays of the present invention can be performed in any of several configurations, which are reviewed extensively in *Enzyme Immunoassay* (Maggio, ed., 1980); Tijssen, *Laboratory Techniques in Biochemistry and Molecular Biology* (1985)). For instance, the proteins and antibodies disclosed here are conveniently used in ELISA, immunoblot analysis and agglutination assays. Particularly preferred assay formats include the immunoperoxidase assay as described in Example 3.

In brief, immunoassays to measure anti-Treponema antibodies or antigens can be either competitive or noncompetitive binding assays. In competitive binding assays, the sample analyte (e.g., anti-Treponema antibodies) competes with a labeled analyte (e.g., anti-Treponema monoclonal antibody) for specific binding sites on a capture agent (e.g., isolated Treponema protein) bound to a solid surface. The concentration of labeled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

A number of combinations of capture agent and labelled binding agent can be used. For instance, an isolated Treponema protein or culture can be used as the capture agent and labelled anti-bovine antibodies specific for the constant region of bovine antibodies can be used as the labelled binding agent. Goat, sheep and other non-bovine antibodies specific for bovine immunoglobulin constant regions (e.g., $\gamma$ or $\mu$) are well known in the art. Alternatively, the anti-bovine antibodies can be the capture agent and the antigen can be labelled.

Various components of the assay, including the antigen, anti-Treponema antibody, or anti-bovine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

Alternatively, the immunoassay may be carried out in liquid phase and a variety of separation methods may be employed to separate the bound labeled component from the unbound labelled components. These methods are known to those of skill in the art and include immunoprecipitation, column chromatography, adsorption, addition of magnetizable particles coated with a binding agent and other similar procedures.

An immunoassay may also be carried out in liquid phase without a separation procedure. Various homogeneous immunoassay methods are now being applied to immunoassays for protein analytes. In these methods, the binding of the binding agent to the analyte causes a change in the signal emitted by the label, so that binding may be measured without separating the bound from the unbound labelled component.

Western blot (immunoblot) analysis can also be used to detect the presence of antibodies to Treponema in the sample. This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-bovine antibodies.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3H$, $^{125}I$, $^{35}S$, $^{14}C$, or $^{32}P$ was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3- dihydrophthalazinediones, e.g., luminol. For a review of various labelling or signal producing systems which may be used, see U.S. Pat. No. 4,391,904, which is incorporated herein by reference.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Some assay formats do not require the use of labelled components. For instance, agglutination assays can be used to detect the presence of the target antibodies. In this case, antigen-coated particles are agglutinated by samples comprising the target antibodies. In this format, none of the components need be labelled and the presence of the target antibody is detected by simple visual inspection.

B. Detection of Treponema Nucleic Acids

As noted above, this invention also embraces methods for detecting the presence of Treponema DNA or RNA in biological samples. These sequences can be used to detect Treponema in biological samples from hooved animals such as cattle. A variety of methods of specific DNA and RNA measurement using nucleic acid hybridization techniques are known to those of skill in the art (see Sambrook et al., supra).

One method for determining the presence or absence of Treponema DNA in a sample involves a Southern transfer. Briefly, the digested DNA is run on agarose slab gels in buffer and transferred to membranes. In a similar manner, a northern transfer may be used for the detection of Treponema mRNA in samples of RNA. Hybridization is carried out using labelled oligonucleotide probes which specifically hybridize to Treponema nucleic acids. Labels used for this purpose are generally as described for immunoassays. Visualization of the hybridized portions allows the qualitative determination of the presence or absence of Treponema genes.

A variety of other nucleic acid hybridization formats are known to those skilled in the art. For example, common formats include sandwich assays and competition or displacement assays. Hybridization techniques are generally described in *Nucleic Acid Hybridization, A Practical Approach* (Hades et al., eds. 1985); Gall & Pardue, *Proc. Natl. Acad. Sci. U.S.A.*, 63:378–383 (1969); and Burnsteil & Jones *Nature*, 223:582–587 (1969).

Sandwich assays are commercially useful hybridization assays for detecting or isolating nucleic acid sequences. Such assays utilize a "capture" nucleic acid covalently immobilized to a solid support and labelled "signal" nucleic acid in solution. The biological sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for detecting Treponema nucleic acids is in situ hybridization. In situ hybridization assays are well known and are generally described in Angerer et al., *Methods Enzymol.*, 152:649–660 (1987). In situ hybridization assays use cells or tissue fixed to a solid support, typically a glass slide. If DNA is to be probed, the cells are denatured with heat or alkali. The cells are then contacted with a hybridization solution at a moderate temperature to permit annealing of labelled Treponema specific probes. The probes are preferably labelled with radioisotopes or fluorescent reporters.

Exemplary nucleic acid sequences for use in the assays described above include sequences from the 16S rRNA sequences disclosed here. For instance, primer and probe sequences derived from the 16S rRNA sequences of the isolates described herein can be used to amplify and identify nucleic acids of bovine Treponema in frozen or formalin-fixed foot tissue, or foot tissue fixed for in situ hybridization. Such 16S rRNA primers are particularly useful for the diagnosis of PDD.

VII. Pharmaceutical Compositions Comprising Treponema

A pharmaceutical composition prepared using anti-Treponema monoclonal antibodies or fragments thereof as well as Treponema cells, proteins or their immunogenic equivalents can be used in a variety of pharmaceutical preparations for the treatment and/or prevention of Treponema infections. The pharmaceutical compositions are typically used to vaccinate hooved animals such as cattle, sheep, goats and other animals infected by Treponema.

The immunogenic whole cell organism, which is employed as the active component of the present vaccines, consists essentially of inactivated PDD-associated Treponema spp. These spirochetes can be isolated from animals affected with PDD, as described above. The spirochetes can be maintained in infected animals, or in suitable nutrient media. The immunogenic spirochetes are typically isolated from skin of affected animals and cultured in defined media.

Another suitable vaccine is a subunit vaccine that elicits antibody and cell-mediated immunity (CMI) to antigens of bovine Treponema. Experimental evidence indicates that CMI is an important component of the protective immune response in cattle. A variety of methods for evaluating the specificity of the helper and cytotoxic T cell response to selected antigens in vitro can be used.

To prepare the vaccine, the spirochetes are first separated from the medium by centrifugation or filtration, or with the use of selective media and the like. The spirochetes can be treated by a number of methods, including chemical treatment, to inactivate them. The spirochetes suspensions can be dried by lyophilization or frozen in an aqueous suspension thereof to yield inactivated whole cells.

The dried or cultured whole cells are then adjusted to an appropriate concentration, optionally combined with a suitable vaccine adjuvant, and packaged for use. Suitable adjuvants include but are not limited to: surfactants, e.g., hexadecylamine, octadecylamine, lysolectithin, dimethyldioctadecylammonium bromide, N,N-dioctadecyl-N'-N-bis(2-hydroxyethyl-propane diamine), methoxyhexadecylglycerol, and pluronic polyols; polyanions, e.g., pyran, dextran sulfate, dipeptide, dimethylglycine, tuftsin; oil emulsions; and alum. Finally, the immunogenic product can be incorporated into liposomes for use in a vaccine formulation, or may be conjugated to polysaccharides or other polymers.

The absolute weight of the deactivated whole cells varies widely, and depends upon factors such as age, weight and physical condition of the subject considered for vaccination. Such factors can be readily determined by the clinician or veterinarian employing animal models or other test systems which are all known to the art. A unit dose of the vaccine is preferably administered parenterally, e.g., by subcutaneous or by intramuscular injection.

For parenteral administration, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella pertussis,* and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma. These proteins can be provided with the vaccine or their corresponding genetic sequence provided as a functional operon with a recombinant vaccine system such as vaccinia virus. The proportion of antigen and adjuvant can be varied over a broad range so long as both are present in effective amounts.

In addition to the Treponema antigen, the vaccine can also include antigens to other ungulate diseases. For example, the vaccine can include antigens to ungulate *Fusobacterium necrophorum, Porphyromonas levii,* and *Dichelobacter nodosus* (the organisms that cause interdigital necrobacillosis, commonly known as foot rot), leptospiral bacteria, bovine respiratory syncytial virus, bovine Herpes virus, bovine diarhhea virus, bovine parainfluenza virus, vesicular stomatitis virus, malignant catarrhal fever virus, blue tongue virus, pseudorabies virus, rabies virus, rinderpest virus, and Clostridia spp. antigen.

Vaccine compositions of the invention are administered to a cattle, sheep, horses, or goats susceptible to or otherwise at risk of infection to induce an immune response against the antigen and thus enhance the patient's own immune response capabilities. Such an amount is defined to be an "immunogenically effective amount." In this use, the precise amounts depend on the judgement of the vaccine manufacturer and prescribing veterinarian and would include consideration of the patient's state of health and weight, the mode of administration, the nature of the formulation, and the like. Generally, on a per-dose basis, the concentration of the Treponema antigen, typically the whole cell, can range from about 10 to about $10^9$ cells per ungulate patient, or 1 $\mu$g to about 100 mg antigen per ungulate patient. For administration to cattle, a preferable range is from about $10^3$ to $10^6$ cells or 100 $\mu$g to 1 mg antigen per unit dose. A suitable dose volume range is 0.5 to 2.0 ml, preferably about 2 ml. Accordingly, a typical dose for subcutaneous injection, for example, would comprise 2 ml containing $10^4$ cells or 500 $\mu$g of antigen.

A variety of vaccination regimens may be effective in immunizing cattle and other animals. For example, ungulate young and adults can both be vaccinated, preferably calves. A second immunization will be given 2–4 weeks after initial immunization. Animals that have been previously exposed to Treponema may require booster injections. The booster injection is preferably timed to coincide with times of maximal challenge and/or risk of abortion. Different immunization regimes may be adopted depending on the judgement of the veterinarian.

Vaccines of the invention may comprise a crude extract of Treponema. Chemically fixed cells can also be used. As noted above, preferred vaccines comprise partially or completely purified Treponema protein preparations. The antigen produced by recombinant DNA technology is preferred because it is more economical than the other sources and is more readily purified in large quantities.

In addition to use in recombinant expression systems, the isolated Treponema gene sequences can also be used to transform viruses that transfect host cells in animals. Live attenuated viruses, such as vaccinia or adenovirus, are convenient alternatives for vaccines because they are inexpensive to produce and are easily transported and administered.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA encoding the Treponema protein or fragments thereof into plasmids so that they are flanked by viral sequences on both sides. The DNA encoding Treponema polypeptides are then inserted into the virus genome through homologous recombination.

Preferentially, a viral vaccine using recombinant vaccinia virus is used. A vaccine prepared utilizing the gene encoding the Treponema protein incorporated into vaccinia virus would comprise stocks of recombinant virus where the gene encoding the Treponema protein is integrated into the genome of the virus in a form suitable for expression of the gene.

EXAMPLES

The following examples are provided by way of illustration only and not by way of limitation. Those of skill in the art will readily recognize a variety of noncritical parameters that could be changed or modified to yield essentially similar results.

Example I
Isolation of Treponema Strains 1-9185MED and 2-1498

Two strains of Treponema isolates were obtained from PDD infected cattle. Biopsies or scrapings from PDD-infected cattle foot tissue lesions were the original source of the cultures. Spirochetes were recovered using selective broth enrichment with rifampin and/or enrofloxacin (see Walker et al., *Vet. Micro.* 47:343–355 (1995)). The cultures were selectively enriched in OTI broth under anaerobic conditions. To obtain pure cultures of Treponema, agar blocks with individual spriochete colonies were removed and placed in OTI broth without antibiotics, propagated for 48 hours, replated to OTI agar, and assessed for purity.

Morphologic characteristics were assessed on Treponema spirochetes grown on OTI and 5% sheep blood agar. Morphologic features were evaluated by darkfield microscopy and transmission electron microscopy.

Enzymatic activity was evaluated using a commercially available system (API ZYM, Bio Merieux, France). Chromosomal DNA was prepared for restriction enzyme digestion, digested with EcoRi, HindIII, and HhaI. SDS-PAGE electrophoresis was used for immunoblot analysis.

Whole cell antigens for production of antisera were obtained using standard procedures from isolates 2-1498 and 1-9185MED. Antisera was prepared by inoculating rabbits (Walker et al., *Am J. Vet. Res.* 49:208–212 (1988)).

Collectively, the morphologic features, antigenic characteristics and the enzymatic activity of the isolates excluded them from all the known genera of spirochetes except for Treponema.

Example II
Clinical and Gross Pathological Description of PDD

This example describes the presentation and symptoms of PDD.

Materials and Methods

A. Herd management

All cows were Holsteins and were housed outdoors all year in drylot soil corrals in the Chino and San Jacinto dairy preserves. Average annual rainfall was 38 cm (range 25 to 89 cm), almost all occurring from January to March. Accumulated fecal waste was scraped from the corrals during summer months and from concrete feedbunk platforms and alleyways periodically throughout the year. Routine foot-bathing was employed on 1 dairy; copper sulfate was used. The size of the herds ranged from 500 to 2200 cows. Approximate age composition of the milking herds was: 50% at 2–3 years; 40% at 4–5 years; and 10% at 6 years and older. Diet consisted of a basic ration of alfalfa hay supplemented with various food commodities and byproducts, such as, cotton seed meal, cotton seed, soybean meal, rolled grains (corn, barley, wheat), almond hulls and vitamin-mineral mixtures.

B. Interviews

Interviews were held with 5 commercial hoof trimmers, 8 veterinarians and 4 dairymen in southern California. These individuals gave historical and general information about approximately 130 dairy herds managed similarly to those investigated. One veterinarian and 1 hoof trimmer had local information relative to the past 17 and 25 years, respectively. Information about PDD was obtained on geographic prevalence, morbidity, age distribution, anatomic location and gross appearance of lesions and response of lesions to treatment.

C. Physical examination of lower limbs

Ninety-three cows in 10 herds were selected for examination because of lameness or grossly visible erosive or papillomatous digital skin lesions. Age was determined by herd record or ear tag information or tooth eruption pattern in a total of 49 cows. The majority of cows (n=82 in 9 herds) were restrained in a tilt chute to facilitate close inspection of all lower limbs. The remaining 11 cows in 1 herd were only visually examined from the rear at a distance of ~1 m as the cows stood in the milking parlor. A total of 350 feet were examined. Feet were washed with water and lesions were photographed and recorded. Visual assessments were also made of corral foot environment (n=7 dairies), trauma of plantar/palmar skin of the feet (n=68 cows) and the size and shape of the interdigital space (IS) of hind and fore feet (n=29 cows). Selected lesions (n=85 in 54 cows) were anaesthetized by locally infiltrating 2% lidocaine into the subcutis and biopsied for laboratory evaluation by either complete excision or by use of a 6 mm diameter punch biopsy instrument (Miltex Instrument Co., Lake Success, N.Y.). Results of histopathologic and bacteriologic evaluations on biopsy materials are published elsewhere. Read et al., *Proc. Int. Sym. Dis. Rum. Digit* 8:156–157 (1994); Read et al., *Vet. Rec.* 130:59–60 (1992); Walker et al., *Vet. Micro.* 47:343–355 (1995).

D. Classification of lesions

Erosive digital skin lesions (n=183 in 93 cows) were classified by anatomic location and gross appearance; and representative lesions (n~85) were examined histopathologically. Pathologic criteria classified these lesions into 3 categories: papillomatous digital dermatitis (PDD), interdigital dermatitis (IDD) and pastern flexural skin fold ulcer (PFSFU) (Read et al., *Proc. Int. Sym. Dis. Rum. Digit* 8:156–157 (1994)). Lesions were histopathologically classified as PDD if they consisted of a circumscribed plaque of eroded acanthotic epidermis attended by parakeratotic papillomatous proliferation profusely colonized by spirochete-dominant bacterial flora, loss of stratum granulosum, invasion of stratum spinosum by spirochetes and infiltration of neutrophils, plasma cells, lymphocytes and eosinophils in dermis. Lesions were classified as IDD if they were located within the IS and had similar histologic character to PDD, except for demarcated margins and papillomatous change. Lesions were not classified as IDD if they were grossly confluent with lesions of PDD. Lesions were classified as PFSFU if they were deep ulcers attended by pyoderma, folliculitis, furunculosis, serum crusting and absence of spirochetes. A possible association between PDD and IDD was examined in 38 feet involved by PDD bordering the interdigital space (IS).

Additional classification was confined to PDD because it was the most prevalent and painful lesion. These additional studies consisted of anatomic distribution of lesions (n=129 in 68 cows) and size, shape, contour, color and surface appearance of lesions (n=134 in 82 cows).

E. Effect of treatments

The effect of various treatments was assessed on a total of 72 lesions of PDD in 35 cows in 3 herds (herds 4 and 5–7). Treatments consisted of procaine penicillin G (G. C. Hanford Manufacturing Co., Syracuse, N.Y.), 18,000 units/kg IM BID for 3 days (7 cows); ceftiofur sodium (Naxcel®, The Upjohn Co., Kalamazoo, Mich.), 2 mg/kg daily for 3 days (14 cows); oxytetracycline (Terramycin—343® Pfizer Animal Health, NY), single topical application of approximately 5 g of soluble powder bandaged directly onto a clean lesion for 7 days (3 cows); formadelhyde (Fisher Scientific, Pittsburg, Pa.), 39% v/v, single topical application (5 cows); hydrochloric acid (Fisher Scientific, Pittsburg, Pa.), 36% v/v, single topical application (4 cows); surgical excision (4 cows); and chlorodifluoromethane, dimethylether (Brand Spray, Stockman Products Ltd., Castledown, Isle of Man, UK), 2 minutes of topical cryogenic spray until lesion and margin were frozen solid and white (1 cow). Two cows which received no treatment served as untreated controls. Therapeutic response was assessed at post treatment days: 7 (4 cows), 7 and 14 (23 cows) and 7, 14 and 21 (7 cows). Therapeutic response was considered complete if there was entire transformation of moist, red, raw, prone-to-bleed, painful surfaces to dry, dark brown, firm, rubbery, keratinacious, non-painful surfaces adherent to underlying pink healthy-appearing skin. The prevalence of recurrent and new lesions was evaluated in 27 of the 35 cows in herds 6 and 7 that had previously responded to treatment 7–12 weeks prior to follow-up examination. Another 6 lesions of PDD in 4 cows in herd 4 were reexamined 5 weeks after total surgical excision.

Results

A. Classification of erosive digital skin lesions

Prevalence of PDD, IDD and PFSFU is shown in Table 1. The great majority (91%) of cows had PDD, whereas smaller numbers had IDD and occasional cows had PFSFU. Some overlap occurred: 19% and 4% of cows with PDD also had separate lesions of IDD and PFSFU, respectively. Also, a great majority (82%) of feet involved by PDD lesions bordering the IS had confluent IDD lesions extending several millimeters into the IS.

B. Clinical signs of PDD

Cows lame with PDD usually exhibited signs of plantar or palmar pain. Severely affected cows were reluctant to move; their affected limb was often held shaking in partial flexion as if in intense pain. Less severely affected limbs rested or bore weight on the toes, and if unresolved, hooves became clubbed with atrophy of the bulbs of the heels. Secondary effects of the lameness included loss of body weight. Little or no diffuse digital swelling was observed. Fissuring and necrosis of the skin of the IS were not seen. Heel horn erosion was commonly seen in feet with or without PDD.

C. Anatomic location of PDD lesions

The anatomic distribution of PDD lesions with respect to affected limb and anteroposterior, mediolateral and digital locations are shown in Tables 1 to 3. Lesions were confined to the digits and were not observed above the level of the dewclaws. Lesions exclusively involved the hind limbs in 56 of 68 (82%) of cows (Table 2). Of these, 24 had right limb involvement, 22 had left limb involvement and 10 had both hind limbs involved. The fore limbs were exclusively involved in 13% of cows and both fore and hind limbs in 5% of cows. Plantar (or palmar) aspects alone were involved in 84% of cows. The dorsal aspect alone was involved in 13% of cows and combined plantar/palmar and dorsal aspects were involved in 3% of cows. No obvious predilection of lesions for medial or lateral digits was observed. Both medial and lateral digits of an affected individual limb were involved in 51% of cows: some (31%) of these lesions opposed each other across the IS, whereas others (19%) confluently involved the entire commissural skin fold bordering the IS. Either medial or lateral digits of an individual limb were involved in 10 and 28% of cows, respectively. With respect to digital site, 76 of 85 (89%) of cows with PDD had lesions involving skin bordering the IS (Table 1); lesions rarely involved the abaxial aspects of the digits. Lesions uncommonly involved skin bordering the base of the bulb of the heel (7 of 85 cows), within the IS (3 of 85 cows), or in plantar pastern flexural skin folds (5 of 85 cows). The lesions affecting the IS were situated on the crest of a corn (2 cows) or involved the entire space from plantar to dorsal aspects (1 cow). Six cows had lesions involving more than 1 site; collectively all 4 sites in table 1 were involved and no pattern was observed. Occasionally, as many as 7 lesions involved an individual limb.

The visual assessments of corral foot environment, trauma of plantar/palmar skin, and size and shape of the IS gave the following results: hind feet were submerged deeper in slurry than fore feet during feeding (due to feedbunk flatform slope), but not at other times; no evidence of consistent trauma was seen in hind or fore feet; and, the dorsal two-thirds of the IS of hind and fore feet was markedly more expansive than the plantar/palmar one-third which was slit-like and difficult to open manually. No obvious differences were noted in the size and shape of the plantar region of the IS compared to its palmer counterpart.

D. Gross appearance of PDD

The size, shape, contour, color and surface characteristics of 134 lesions are presented in Table 3. The majority of lesions were medium to large, namely, 2–6 cm across at their greatest dimension (88%), circular to oval (90%), raised (64%), and variable in color and in degree of papillary proliferation. Washed surfaces were typically either extensively red and granular (31%) or a composite of white-yellow, grey, brown and/or black papillary areas interspersed with red granular areas (42%). Lesions extensively covered by large numbers of papillae comprised 27% of the total. Papillae were usually filiform; their caliber was about 0.5–1 mm and their length varied from 1 mm to 3 cm. Small lesions (1 cm across) were uncommonly observed (12%) and they had similar features to medium and large lesions except that most had extensively red granular surfaces. A small proportion of large lesions were "U" shaped because they involved the entire commissural fold of skin that borders the plantar/palmar IS.

Regardless of size, shape and contour, lesions were characteristically circumscribed or delineated by a discrete line of raised hyperkeratotic skin often bearing erect hairs 2–3 times longer than normal. They were also partially to completely alopecic and their surfaces were moist, prone to bleed and intensely painful to touch. Lesions proximal and adjacent to the heel bulb characteristically expanded to involve and replace perioplic horn. Some lesions undermined the horn of the heel bulb for a distance of several millimeters but suppurative underrunning of horn was not observed. Defects in the wall were observed in 2 cows and, in both, the defects were related to proximal PDD lesions involving the coronary band.

The clinical and gross pathologic features of PDD described here are essentially identical to those reported for digital dermatitis (DD) in Canada, Europe, England and Ireland (Basset et al., *Vet. Rec.* 126:164–165 (1990); Blowey et al., *Vet. Rec.* 135, 115–117 (1994); Blowey et al., *Vet. Rec.* 122:505–508 (1988); Borgmann et al., *Can. Vet.* 37:35–37 (1983); Brizzi, *Proc. Annu. Conf. Am. Assoc. Bov. Pract.* 26:33–37 (1993); Cheli et al., *Proc. Int. Meet. Dis. Cattle* 8:208–213 (1974); Gourreau et al., *Le Point Vet* 24:49–57 (1992); Zemljic, *Proc. Int. Sym. Rum. Digit* 8:164–167 (1994)), interdigital papillomatosis in New York (Rebhun, et al., *J. Am. Vet. Med. Assoc.* 177:437–440 (1980)) and verrucose dermatitis and digital papillomatosis in Japan (Kimura et al., *J. Vet. Med. Jpn.* 46:899–906 (1993)). These features also serve to differentiate PDD from other specific inflammatory diseases of the digital skin of cattle. The most striking distinguishing feature noted in the present study was the anatomic predilection of lesions for hind limbs and skin-horn junctions, especially those bordering the plantar aspect of the IS. Lesions only rarely involved the IS per se. Such selective vulnerability appears to be highly distinctive because it is not reported as a hallmark of other bovine digital skin diseases (Blowey, In *Practice*, 85–90 (1992); Greenough et al., *Lameness in Cattle* pp. 151–169 (Weaver ed., 2nd ed. 1981); Weaver, *Agri-Practice* 9:34–38 (1988)). In addition, other characteristic features reported here include the propensity of PDD lesions to develop filiform papillae and that the lesions were intensely painful to touch, prone to bleed and demarcated by a raised line of hyperkeratotic skin, often bearing hypertrophied hairs. Overall, these features indicate that PDD, like DD (Blowey et al., *Vet. Rec.* 122:505–508 (1988); Greenough et al., *Lameness in Cattle* pp. 151–169 (Weaver ed., 2nd ed. 1981)) represents a single specific disease entity.

Interdigital necrobacillosis (footrot) differs from PDD because it primarily involves interdigital skin and is characterized by fissuring, caseous necrosis of subcutis and diffuse digital swelling (Edmondson, *Proc. Int. Meet Dis. Cattle* 8:208–213 (1990); Greenough et al., *Lameness in Cattle* pp. 151–169 (Weaver ed., 2nd ed. 1981)). Interdigital dermatitis (IDD) also primarily involves interdigital skin and causes only mild lameness (Greenough et al., *Lameness in Cattle* pp. 151–169 (Weaver ed., 2nd ed. 1981); Weaver,

*Agri-Practice* 9:34–38 (1988)). Although IDD has been widely considered a separate entity (Weaver, *Agri-Practice* 9:34–38 (1988)), its identity has been recently questioned because, histopathologically, it shares some features in common with DD (Blowey, *Proc. Int. Sym. Dis. Rum. Digit* 8:142–154 (1994)); and PDD (Read et al., *Proc. Int. Sym. Dis. Rum. Digit* 8:156–157 (1994)) and it has been associated with DD in the field (Blowey, *Proc. Int. Sym. Dis. Rum. Digit* 8:142–154 (1994); Toussaint et al., *Vet. Med. Review* 2:223–247 (1971)). In this study it was found that 82% of feet that had PDD bordering the IS also had contiguous IDD. These observations, as well as the recent isolation of an identical spirochete in PDD and IDD lesions (Walker et al., *Vet. Micro.* 47:343–355 (1995)), indicate that further study is required to clarify the interrelationships of these 2 entities.

A few cows in this study had involvement of flexural skin folds of the pastern by either deep ulcers or PDD. The 2 conditions appeared histologically different (Read et al., *Proc. Int. Sym. Dis. Rum. Digit* 8:156–157 (1994)) but their predilection for the same site suggests some commonality in their pathogenesis. Similar ulcers or fissures are reported to occur on the lower limbs of cattle involved by diffuse exudative dermatitis housed under prolonged wet unhygienic conditions (McLennan et al., *Aust. Vet. J.* 68:76–77 (1991)).

E. Effect of treatments

PDD lesions were highly responsive to parenteral or topical antibiotics or topical caustic chemicals (Table 4). Sixty-five of 72 lesions involving 30 of 35 cows treated with antibiotics or caustics showed a complete therapeutic response by post-treatment (PT) day 21. This was characterized by complete transformation of moist, red, raw, painful prone-to-bleed surfaces to dry, dark brown, non-painful, tough rubbery keratinacious surfaces. The keratinacious layer was tightly adherent to underlying white-pink healthy-appearing skin. These changes were observed in 66% of cows by PT day 7. By PT day 21, diminution in size and partial restoration of hair growth were also observed.

Mean therapeutic response times as determined by desiccation and keratinization of surfaces and absence of pain were slightly longer for cows treated parenterally with ceftiofur (11.1±4.5 days, n=13) compared to those treated parenterally with penicillin (8.2±2.5 days, n=7) or topical applications of oxytetracycline (7 days, n=3), formaldehyde (7 days, n=5) or hydrochloric acid (7 days, n=2). No consistent differences in response time were observed in lesions of different sizes or at different sites.

Incomplete responses occurred in 2 cows treated with ceftiofur and in 2 other cows treated with hydrochloric acid. In 1 of the 2 ceftiofur-treated cows, 2 large raised papillary lesions on one limb were refractory over a PT period of 73 days despite a second course of antibiotics (parenteral penicillin); whereas 6 similar medium-sized papillary lesions on the ipsilateral limb were completely responsive to the first treatment by PT day 7. In the 2 hydrochloric acid-treated cows, the incomplete responses were characterized by persistence of small painful deep ulcers. The lesion treated with cryogenic spray did not respond.

The prevalence of recurrent and new lesions in 27 treated cows in 3 herds is shown in Table 5. Lesions recurred in 9 cows and new lesions developed in 4 other cows that had previously responded completely to treatment, 7–12 weeks prior to follow-up examination. Two cows that had recurrent lesions also had new lesions. The combined rate of recurrence and new-lesion development in treated cows was 48%. Recurrence and new-lesion-development were observed in cows treated with either ceftiofur or penicillin. New lesions occurred in cows treated with hydrochloric acid and recurrent lesions occurred in cows treated by surgical excision.

The epidemiologic observations indicate that PDD behaves as an infectious disease, a view also held with respect to DD (Brizzi, *Proc. Annu. Conf. Am. Assoc. Bov. Pract.* 26:33–37 (1993); Gourreau et al., *Le Point Vet* 24:49–57 (1992); Nutter et al., *Vet. Rec.* 126:200–201 (1990)). The geographic spread, evidence of contagion, high prevalence in young cows and high within-herd morbidity observed here are consistent with this view. In addition, the marked sensitivity of PDD lesions to parenteral or topical (Britt et al. *J. Am. Vet. Med. Assoc.* 209:1134–1136 (1996)) antibiotics as well as the presence of intralesional invasive spirochetes (Read et al., *Proc. Int. Sym. Dis. Rum. Digit* 8:156–157 (1994); Read et al., *Vet. Rec.* 130:59–60 (1992)), provide convincing evidence that bacteria may play an important role in the pathogenesis of the disease. Also, the histologic similarity of PDD to yaws, a papillomatous condition of the feet and lower legs of people living in the tropics caused by *Treponema pallidum* subspecies *pertenue* (Engelkens et al., *Int. J. Dermatol* 30:77–83 (1991)), adds further support.

In this study, the incidence of PDD in southern California increased in late spring to early summer. This was later confirmed by an epidemiologic survey (Rodriguez-Lainz et al., *J. Am. Vet. Med. Assoc.,* 209:1464–1467 (1996)). A subsequent epidemiologic case study of 57 dairies in southern California revealed that muddiness of corrals was strongly linked to high PDD prevalence herds (Rodriguez-Lainz et al., *Prev. Vet. Med.* 28:117–131 (1996)). In the UK and Europe, poor feet hygiene has also been linked with the occurrence of DD in winter-housed cattle (Blowey, *Proc. Int. Sym. Dis. Rum. Digit* 8:142–154 (1994); Blawey et al., *Vet. Rec.* 122:505–508 (1988); Nutter et al., *Vet. Rec.* 126:200–201 (1990)). Suggested predisposing factors include prolonged contact of the lower limbs with manure-rich stale slurry (Blowey, *Proc. Int. Sym. Dis. Rum. Digit* 8:142–154 (1994)), a foot environment similar to that which we observed during the rainy season here. However, our observation was confounded by another observation in this study, namely, that some outbreaks occurred in late fall, approximately 5 months after the corrals had largely dried out. Others investigators agree that predisposing factors for outbreaks of DD are not always clearly evident (Weaver, *Proc. 7th Int. Symp. Dis. Rum. Digit;* Zemljic, *Proc. Int. Sym. Rum. Digit* 8:164–167 (1994)) and still others report outbreaks associated with excellent hygiene in housed and pastured cattle. Gourreau et al., *Le Point Vet* 24:49–57 (1992). As well as muddiness of corrals, another risk factor revealed by the California case-control study was the introduction of heifer replacements (Rodriguez-Lainz et al., *Prev. Vet. Med.* 28:117–131 (1996)). Other investigators in the U.S. and Europe also attribute the spread of PDD/DD to sharing of cows among herds (Gourreau et al., *Le Point Vet* 24:49–57 (1992)) or introduction of sound heifers from affected herds (Brizzi, *Proc. Annu. Conf. Am. Assoc. Bov. Pract.* 26:33–37 (1993); Nutter et al., *Vet. Rec.* 126:200–201 (1990); Weaver, *Proc. 7th Int. Symp. Dis. Rum. Digit;* Whittier, *Dairy* 12–13 (1988)).

The reason why PDD or DD lesions have a high predilection for plantar/palmar skin bordering the IS is not known. This visual assessment of corral underfoot environment showed that hind limbs were exposed to deeper slurry during feeding than were forelimbs, but the significance of this was not assessed because the preferential site for PDD is almost at ground level. With respect to the possibility of trauma, no evidence was found of continual abrasion of either plantar or palmar digital skin. Visual evaluation of the size and shape of the IS clearly showed that plantar and palmar regions were slit-like because the bulbs were in close opposition. The plantar/palmar regions of the IS were, therefore, much more prone to being continually moist compared to their more open dorsal counterparts. Since IDD, PDD/DD are favored by a continually moist foot environment (Blowey, *Proc. Int. Sym. Dis. Rum. Digit* 8:142–154 (1994); Greenough et al., *Lameness in Cattle*, pp. 151–169 (Weaver ed., 2nd ed. 1981); Rodriguez-Lainz et al., *J. Am. Vet. Med. Assoc.*, 209:1464–1467 (1996); Weaver, *Agri-Practice* 9:34–38 (1988)), this observation may help to explain why lesions of these entities occur more frequently at these locations than elsewhere. In this connection, it is significant that a study on the natural evolution of DD found that 90% of early erosive lesions began at the plantar border of the IS and then, by proximal local extension, developed into typical strawberry-like lesions (Morterello et al., *Proc. Int. Sym. Dis. Rum. Digit* 8:177–179 (1994)). The plantar/palmar region of the IS may therefore possess special conducive factors for the development of PDD, one of which may be a moisture retention property.

In the present study, PDD was observed most frequently in lactating heifers, a finding also reported by other investigators in the U.S. (Weaver, *Proc. 7th Int. Symp. Dis. Rum. Digit*) and Europe (Blawey et al., *Vet. Rec.* 122:505–508 (1988); Brizzi, *Proc. Annu. Conf. Am. Assoc. Bov. Pract.* 26:33–37 (1993); Gourreau et al., *Le Point Vet* 24:49–57 (1992)). The reason for this apparent age prevalence is unknown but raises the possibility that infected cows become immune as they age. Against this, however, is observation of recurrence or new-lesion-development in 48% of cows reexamined 7–12 weeks after a complete therapeutic response was observed.

TABLE 1

Classification and anatomic location of 183 erosive digital skin lesions in 93 Holstein cows in 10 California dairy herds.

| Lesion/Anatomic Site | No. of cows¶ | No. of lesions§ |
|---|---|---|
| A. Papillomatous digital dermatitis: | | |
| 1) Proximal border of interdigital space | 76 | 123 |
| 2) Proximal border of heel bulb | 7 | 11 |
| 3) Interdigital space | 3 | 3 |
| 4) Plantar pastern | 5 | 10 |
| B. Interdigital dermatitis | 18 | 27 |
| C. Pastern flexural skin fold ulcer | 9 | 9 |

¶ = 25 of the 76 cows in category A1 also had lesions listed in other categories: A2 (2 cows), A2 and A4 (2 cows), A3 (2 cows, B (16 cows) and C (3 cows).
§ = A great majority of A1 lesions extended a few millimeters distally to involve the skin of the interdigital space.

TABLE 2

Anatomic location of 129 lesions of papillomatous digital dermatitis in 68 Holstein cows in 8 California dairy herds.*

| | Cows | | Lesions | |
|---|---|---|---|---|
| Anatomic location | n | % | n | % |
| Limb: | | | | |
| Right hind | 24 | 35 | 41 | 31 |
| Left hind | 22 | 32 | 38 | 29 |

TABLE 2-continued

Anatomic location of 129 lesions of papillomatous digital dermatitis in 68 Holstein cows in 8 California dairy herds.*

| | Cows | | Lesions | |
|---|---|---|---|---|
| Anatomic location | n | % | n | % |
| Right and left hind | 10 | 15 | 27 | 21 |
| Hind and Forelimbs | 3 | 5 | 11 | 9 |
| Forelimbs | 9 | 13 | 13 | 10 |
| Plantar/palmar/dorsal: | | | | |
| Plantar/palmar | 57 | 84 | 115 | 88 |
| Dorsal | 9 | 13 | 13 | 10 |
| Plantar/palmar and dorsal | 2 | 3 | 2 | 2 |
| Medial/lateral digits/axial: ¶ | | | | |
| Medial | 7 | 10 | 9 | 6 |
| Lateral | 19 | 28 | 31 | 24 |
| Biaxial | 21 | 31 | 50 | 39 |
| Axial | 8 | 12 | 15 | 12 |
| Extensive (axial and medial and/or lateral) | 13 | 19 | 25 | 19 |

* = Herds 2, 4 to 10. In herds 1 and 3, all 4 feet were not systematically examined.
¶ = Pertaining to an individual limb.

TABLE 3

Gross appearance of 134 lesions of papillomatous digital dermatitis in 82 Holstein cows in 9 California dairy herds.*

| | Number of lesions | | | | | |
|---|---|---|---|---|---|---|
| | Small (1 cm)¶ | | Medium (2 cm) | | Large (3–6 cm) | |
| Lesion characteristic | n | (%) | n | (%) | n | (%) |
| Shape: | | | | | | |
| Circular/oval | 16 | (12) | 52 | (39) | 53 | (39) |
| U-shaped | 0 | | 0 | | 12 | (9) |
| Linear | 0 | | 0 | | 1 | (1) |
| Contour: | | | | | | |
| Concave | 4 | (3) | 0 | | 0 | |
| Flat | 5 | (4) | 22 | (16) | 17 | (13) |
| Raised | 7 | (5) | 30 | (22) | 49 | (37) |
| Color and Surface: | | | | | | |
| Red, granular | 8 | (6) | 16 | (12) | 17 | (13) |
| Red, granular with yellow/grey papillary areas | 5 | (4) | 21 | (16) | 29 | (22) |
| Grey/brown/black, extensively papillary | 3 | (2) | 15 | (11) | 20 | (14) |

* = Herds 1, 2, 4 to 10. In herd 3, lesions were not systematically examined.
¶ = Greatest dimension across lesion, rounded up/down to nearest cm.

TABLE 4

Effect of various treatments on 72 lesions of papillomatous digital dermatitis in 35 Holstein cows in 3 California dairy herds.*

| | No. of cows assessed | | No. of lesions assessed# | |
|---|---|---|---|---|
| Treatment | Treated | Responded | Treated | Responded |
| Antibiotics | | | | |
| Penicillin G procaine IM | 7 | 7 | 9 | 9 |

TABLE 4-continued

Effect of various treatments on 72 lesions of papillomatous digital dermatitis in 35 Holstein cows in 3 California dairy herds.*

| Treatment | No. of cows assessed | | No. of lesions assessed# | |
|---|---|---|---|---|
| | Treated | Responded | Treated | Responded |
| Ceftiofur IM | 15 | 13 | 44 | 41 |
| Oxytetracycline, topical | 3 | 3 | 4 | 4 |
| Topical Caustics | | | | |
| Formaldehyde (39%) | 5 | 5 | 8 | 8 |
| Hydrochloric acid (35%) | 4 | 2 | 6 | 3 |
| Physical agent | | | | |
| Cryogenic spray | 1 | 0 | 1 | 0 |

\* = Herds 5 to 7
# = Therapeutic response was assessed at post-treatment days: 7 (5 cows); 7 and 14 (23 cows); and 7, 14 and 21 (7 cows.). Fifty-five lesions bordered the interdigital space; 9 bordered the base of the heel bulb and 8 involved flexural plantar pastern skin fold.

TABLE 5

Prevalence of recurrent and new lesions of papillornatous digital dermatitis in 27 Holstein cows in 3 herds* that previously completely responded to treatment 7–12 weeks prior to follow-up examination.

| Treatment | Responsive¶ | | Recurrent# | | New§ | |
|---|---|---|---|---|---|---|
| | Cows n | Lesions n | Cows n | Lesions n | Cows n | Lesions n |
| Antibiotics | | | | | | |
| Pencillin G procain IM | 3 | 3 | 1ˡ | 1 | 2 | 4 |
| Cetifur IM | 11 | 30 | 4ˡ | 6 | 2 | 2 |
| Topical Caustics | | | | | | |
| Formaldehyde (39%) | 6 | 8 | 0 | 0 | 0 | 0 |
| Hydrochloride acid (36%) | 3 | 4 | 0 | 0 | 2 | 3 |
| Surgical excision | 4 | 6 | 4 | 6 | 0 | 0 |
| Totals | 27 | 51 | 9 | 13 | 6 | 9 |
| % | | | 33 | 26 | 22 | 18 |

\* = Herds 4, 6 and 7
¶ = Criteria for complete therapeutic response were: absence of evincible pain and transformation of exudative surfaces to dry brown/black rubbery hyperkeratotic layers adherent to white-pink healthy-appearing skin.
# = Recurrence of a lesion at a previously responsive affected site.
§ = Occurrence of a lesion at a previously non-affected site
ˡ = 1 cow also had a new lesion

Example III
Transmission of PDD

Transmission of PDD can be used to demonstrate that vaccinated cattle can be challenged with PDD. Thus, this is a useful technique to demonstrate the efficacy of PDD vaccines.

Materials and Methods

A. Animals

Eight 4- to 5-month-old Holstein calves were obtained from a multi-source calf raising facility in Chino, Calif. They were moved to the San Bernardino branch laboratory of the California Veterinary Diagnostic Laboratory System where they were housed on concrete floors in environmentally controlled isolation rooms for 49 to 111 days. Seven were female and 1 was a castrated male. Each calf was fed approximately 2 kg of alfalfa hay and 1.5 kg of mixed grain per day and had ad libitum access to water. Floors were scraped and hosed clean daily.

B. Experimental Design

Two experiments were performed. In experiment I, both hind feet of 6 principals (calves 1–6) and the left hind foot of 2 control (calves 7 & 8) were constantly maintained in a moist and relatively anaerobic environment from 6 to 10 days pre-inoculation to the end of the experimental periods. The foot environment was achieved by wrapping the lower limb, from the sole to the upper third of the metatarsus, with a polyethylene sheet, orthopedic cotton and elastic bandage, in that order, followed by placing the foot inside an impervious plastic boot. The bandages were sprayed with water until saturated 3 times each day. In experiment II, calves 7 and 8 were utilized as principals, after an acclimation period of 3 weeks following the end of experiment I. No attempt to constantly maintain moist and anaerobic foot conditions was performed. The right hind foot of each calf was inoculated and lightly bandaged keep the inoculum in place. No boots were applied.

C. Inoculations

Skin of one hind foot of each principal (left hind in calves 1–6 in experiment I and right hind in calves 7 and 8 in experiment II) was inoculated at 2 anatomic sites: distal skin-horn junction of the dewclaw and proximoaxial skin-horn junction of both heels adjacent to the plantar interdigital space. In 2 principals (calves 1 and 2), skin at the lateral heel site was mechanically scarified by use of sterile sand paper immediately before inoculation: Inoculum consisted of chilled homogenate of PDD lesions which were excised from clinically affected cows 3 to 4 hours prior to use. Activity and identity of the clinical lesions were confirmed by dark field examination and histopathology. Inoculation was performed by placing approximately 0.5 g of the homogenate on each skin site. Inoculum was held in place by a small (1×1 cm) piece of sterile cotton gauze moistened with sterile saline covered by the prescribed wraps. Inoculation was repeated 7–10 days after the first inoculation, namely, on PID 7 to 10.

D. Observations

Calves were observed daily for signs of well-being, foot swelling and lameness. Hind feet were examined weekly for gross lesions. Lesions were recorded and selected sites were superficially scraped for darkfield microscopy (calves 1–6) or punch biopsied for bacteriological culture (Walker et al., Vet. Microbiol. 47:343– 355 (1995)) (calves 1 and 2) and histopathology (calves 1–6). Selected control skin sites were sampled for darkfield microscopy (calves 1, 3–6) and histopathology (calves 7 and 8 in experiment I and II). Calves were sampled for blood serum on PID 1 and at 2 weekly intervals thereafter. Serum was stored at −20° C. until assayed by ELISA for levels of antibody to spirochetes associated with naturally occurring PDD. Experiments were terminated when lesions spontaneously resolved, either completely (calves 1–4) or partially (calves 5 and 6).

Results

A. Experiment I

All principals developed lesions of PDD and all lesions developed at inoculation sites. Nine of 10 dew claw sites and 2 of 6 heel-interdigital sites developed lesions. In two principals (calves 1 & 2), non-inoculated medial dew claw skin developed lesions 7 days after lesions were observed in their lateral inoculated counterparts. The number of lesions observed at an inoculation site varied from 1 (calves 3 and 4), 2 to 3 (calves 2, 5 & 6) and 5 (calf 1). The size of lesions varied from 2 to 3 millimeters to 3 centimeters across at their greatest dimension. Small lesions generally involved dew claw sites and large lesions at heel-interdigital sites. Most dew claw lesions became grossly apparent at PID 14 to 16

(7 of 11). The remainder of the dew claw lesions and the heel-interdigital lesions were first observed at PID 21. Lesions generally increased in size during the first 2 to 5 weeks after their appearance. Thereafter, they usually remained static or gradually decreased in size. In one principal, 5 lesions manifested at the heel-interdigital site at various times over a 5-week-period, sometimes resolving and at other times recrudescing. Six dew claw lesions and the heel-interdigital lesions spontaneously resolved. Resolution time varied from 33 to 94 days. Five other dew claw lesions (calves 4–6) were not observed to resolve because the experiments were terminated at PID 35–54 while the lesions were still active. Resolution was characterized by centripetal shrinkage, desiccation, keratosis and loss of pain.

The gross pathologic character of the lesions was uniform irrespective of site. Early development (PID 14–21) was characterized by matting of the hairs with dark brown viscid exudate, easily plucked hairs and a diffusely red moist painful skin surface. By PID 28–35, alopecia was complete, the eroded surface was red and finely granular and a raised epidermal collar delineated the lesion from surrounding normal skin. No lesions developed papilliform proliferations. Local extension of lesions to involve structures other than skin occurred in 1 principal (calf 2). In this calf, large lesions encroached upon and replaced perioplic heel horn and, by PID 35, atrophy of heel and clubbing of the hoof was evident.

The histopathologic character of the lesions was also uniform irrespective of site. Variation was observed in the biopsies according to severity and chronicity. Lesions in biopsies taken PID 16 to 21 were characterized by: diffuse loss of stratum corneum; dense colonization of parakeratotic epidermis and invasion of superficial stratum spinosum and eroded dermal papillae by long slender spiral bacteria; congestion, thrombosis, suppuration and necrosis of superficial papillary dermis; acanthosis; and lymphoplasmacytic perivascular dermatitis. In 7 biopsies taken PID 42 to 71, lesions were similar but more proliferative in character with focal areas of intense bacterial colonization and inflammation interspersed with areas of epidermal parakeratosis and hyperkeratosis. Dark field microscopy findings and bacteriologic culture results of lesions were characteristic of PDD.

No gross or histopathologic lesions were observed in the control calves (calves 7 and 8).

B. Experiment II

No gross or histologic lesions were observed in the calves of this experiment (calves 7 and 8).

The transmission of PDD achieved in this study corroborates for the first time previously reported anecdotal field observations that the disease is contagious.

The highly repeatable transmission achieved under controlled environmental foot conditions, as well as the failure to transmit outside those conditions, infers that PDD is a multifactorial disease with environmental as well as infectious causative factors. These experiments identified 2 environmental factors, namely, constant moisture and lack of access to air. These factors are consistent with findings in a recent epidemiologic study of PDD in California dairies, namely, that deep muddy corrals constitute a high risk for contracting the disease.

Example IV

Immnunoperoxidase Staining Protocol for PDD in Formalin-fixed, Paraffin-embedded Tissue The following protocol was used to determine whether ungulate tissue is infected with Treponema by detecting Treponema antigen with a specific antibody. The tissue to be tested was embedded in paraffin and then sectioned for binding with a specific antibody in situ. The specific antibody was detected with a labeled secondary antibody. The labeling pattern was then visualized using a microscope. This protocol was used as a diagnostic protocol for PDD.

A. Equipment

Micropipette, variable delivery

Microprobe Staining Station

Scale

Water Bath, 37° C.

B. Materials

AEC Substrate, Single Solution (Zymed catalog #00-1111)

Bluing Reagent (Richard Allan catalog #7301)

Coverslips, 24×20 (Fisher catalog #12-548-5J)

Crystal Mount, Biomeda (Fisher catalog #BM-M03)

Hematoxylin Solution, Mayer's (Sigm a catalog #MHS-16)

Hydrochloric Acid, 1 N (Fisher catalog #SA48-1)

Hydrogen Peroxide, 30% (Sigma catalog #H-1009)

Methanol, Absolute (Fisher catalog #A433-4)

Microscope Slides, Probe-On-Plus (Fisher catalog #15-188-51)

Mounting Medium, Accu-Mount 60 (Baxter catalog #M7630-1)

Pepsin (Sigma catalog #P7000)

Phosphate Buffered Saline (Sigma catalog #1000-3)

Positive Control Tissue

Primary Antibodies, Specific (hyperimmune rabbit sera to Treponema strains 1-9185MED and 2-1498; Walker et al., Vet. Microbiol. 47: 343–355 (1995)) and Non-Specific (normal rabbit serum, Vector Elite)

Rabbit IgG Elite Detection Kit (Vector catalog PK6101)

Reagent Alcohol, ABsolute (Fisher catalog #A962-4)

Tween 20 (Sigma catalog #P-1379)

Xylene (Fisher catalog #X3$^P$)

C. Reagent Preparation

Pepsin solution: 0.6 g pepsin was added to 150 ml 0.01 N hydrochloric acid (1.5 ml 1 N HCl+150 ml deionized water). The solution was placed in a 37° C. water bath for 30 minutes before use.

Hydrogen peroxide solution, 3%: 15 ml 30% hydrogen peroxide was added to 135 ml absolute methanol.

Phosphate buffered saline (PBS): one package PBS was added to one liter deionized water. Check pH and, if necessary, adjust to 7.4.

PBS/Tween: 600 $\mu$l (12 drops) Tween was added to 240 ml BPS. The 10×Automation Buffer (100 ml) in deionized water (900 ml) may substitute for PBS/Tween.

PBS/Tween/Alcohol: 100 ml reagent grade absolute alcohol was added to 900 ml PBS/Tween.

Normal goat serum, Vector Elite: Three drops stock normal goat serum was added to ten ml PBS/Tween.

Primary antibodies: Diluted in PBS to 1:400.

Biotinylated secondary antibody, Vector Elite: Three drops stock normal goat serum were added to ten ml PBS/Tween. Mixed, one drop biotinylated antibody added.

ABC reagent, Vector Elite: Two drops of reagent "A" were added to five ml PBS/Tween. Mix and add two drops reagent "B", mix immediately. ABC reagent was allowed to stand 30 minutes before use.

AEC Single Solution: Used directly from bottle. If solution is colored, discard.

D. Procedure

For each specific primary antibody, two slides from each paraffin block to be tested and two positive control slides are needed. Tissue was sectioned at three to four microns, and mounted on far right-hand side of "Probe On Plus" microscope slides. One slide was labeled with the specific primary antibody name and dilution (i.e., anti-Treponema antibody 1-9185 1:400) and the other with the nonspecific primary antibody name and dilution (i.e., NRS 1:400). Both slides were labeled with the case accession and block number (or control lot number), detection system (i.e., ERK), and run date. The sections were allowed to dry overnight. Unless otherwise noted, all incubations and reagents are used at room temperature. The buffers and detection kit were stored in a refrigerator. The buffers are checked for gross contamination before use. Primary antibodies are stored at −7° C.

The slides were placed in a conventional slide holder, and deparaffinized for five minutes in each of three changes of xylene. The slides are placed in two changes of reagent grade absolute alcohol, allowing three minutes for each change. The slide holder was agitated for the first ten seconds of each of these and subsequent reagent changes, excluding those changes where the Microprobe handle was used.

The slides were immersed in 3% hydrogen peroxide solution for ten minutes. The sections were rehydrated on the slides for two minutes in each change of 95, 80% and 70% reagent grade alcohols, and two changes of deionized water.

The slides were placed in pepsin solution for 15 minutes at 37° C. The slides were rinsed in four changes of deionized water, one minute each change.

The slides were placed face to face (section to section) in the Microprobe handle. A blank Probe-On-Plus slide was used to pair-up any unpaired slides. If multiple stains were being performed, record which slide in the Microprobe handle receives which primary antibody.

Rinse/blot cycles were performed using PBS/Tween and paper towels. Rinse/blot cycles followed using PBS/Tween/Alcohol. At the end of these rinse/blot cycles, all air bubbles should have been removed from between the slides.

Normal goat serum was applied to the slides for 20 minutes. All reagents should be applied to the edge of each set of slides to ensure that the all parts of the tissue receive reagent. To compensate for evaporation, slides were allowed to stand in a pool of the reagent, or placed in a moist chamber.

Normal goat serum was blotted from the slides and the specific and non-specific primary antibodies applied for one hour. Ten blot/rinse cycles were performed with PBS/Tween/Alcohol.

Biotinylated secondary antibody was applied to the slides for 15 minutes. Blot/rinse cycles were performed with PBS/Tween/Alcohol.

ABC reagent was applied for 15 minutes. Ten blot/rinse cycles were performed with PBS/Tween.

AEC reagent was applied for three minutes. Three blot/rinse cycles were performed with deionized water, slides were transferred to conventional slide holder, and deionized water was applied for three minutes.

The slides were counterstained with filtered Mayer's hematoxylin for 90 seconds and then rinsed for two minutes in running tap water.

The slides were blued for one minute in hematoxylin bluing reagent and rinsed in two changes of deionized water, two minutes each.

Crystal/Mount medium was applied over sections and the slides were placed on a 70–80° C. hot plate for a minimum of ten minutes. The slides were removed from hot plate and allow to cool. The coverslip was mounted with Accu-Mount mounting medium.

The control and test slides were evaluated for staining. Only the specific primary antibody slide should show red staining of the antigen being stained.

Example V

Vaccine Preparation and Immunization

A. Origin and Cultivation of PDD-Associated Treponema spp.

PDD-associated Treponema spp. have been recognized as likely etiologic agents involved in the pathogenesis of PDD. These spirochetes were first isolated and cultivated in oral treponeme isolation (OTI) broth at 37° C. (Walker et al., *Vet. Microbiol.* 47:343–355 (1995)). In addition, a modified Barbour-Stoenner Kelly (BSK) medium was used to culture the organisms at 30–37° C. in microaerophilic to anaerobic conditions to a density between $1 \times 10^4$ to $1 \times 10^9$ spirochetes/ml. The modified medium was prepared by the addition of 0.15% agarose (Seakem LE; FMC Corp., Rockland, Me.) to the BSK medium. The BSK medium was prepared as disclosed by Barbour, Isolation and cultivation of Lyme disease spirochetes, in Lyme Disease, First International Symposium, pp. 71–75 (Steele et al., eds., (1984)).

B. Vaccine Preparation and Immunization

The vaccine was prepared by suspending organisms to a specific optical density in 0.5% formalized physiological saline solution. This cellular preparation was devoid of viable cells. Neither culture or the injection of the cell preparation used in rabbits provided evidence of viable spirochetes. Non-pregnant, female, New Zealand White rabbits were injected with a single dose of vaccine subcutaneously followed by 5 intravenous doses of vaccine at 3 day intervals. Rabbits were bled prior to immunization and one week after the last injection. No adjuvant was used. For vaccination of male Holstein calves, spirochete antigen was prepared by growing spirochetes in OTI broth for 48 hours at 37° C. Cultures were washed in physiological saline solution and suspended to a concentration equivalent to an $OD_{550}$ of 0.4 in 0.5% formalized saline. The suspension was stored at −70° C. until used. Calves were initially given 1 subcutaneous injection followed by 6 intravenous immunizations at 3 day intervals. Calves were bled prior to immunization and one week after the last vaccination. No adjuvant was used.

TABLE 6

Active Immunization of Rabbits with PDD-associated *Treponema spp.* strain 1-9185-MED and 2-1498 PDD.

| | 1-9185MED | 2-1498 |
|---|---|---|
| Pre-vaccination ELISA titer to homologous spirochete | <1:100 | 1:400 |
| Post-vaccination ELISA titer to homologous spirochete | >1:6400 | >1:6400 |

Titers are determined as the lowest dilution at which the optical density was two times that of the optical density obtained when no serum was used in the ELISA.

TABLE 7

Active immunization of calves with PDD-associated *Treponema spp.* strain 1-9185 MED and 2-1498.

|  | 1-9185MED | 2-1498 |
|---|---|---|
| Pre-vaccination ELISA titer to homologous spirochete | 1:200 | 1:200 |
| Post-vaccination ELISA titer to homologous spirochete | >1:6400 | 1:6400 |

Titers are determined as the lowest dilution at which the optical density was two times that of the optical density obtained when no serum was used in the ELISA.

The data summarized in Table 7 indicates that a repeated immunization with PDD-associated Treponema spp results in boosting the levels of serum antibodies to those spirochetes in the cow. The use of a plurality of vaccinations is expected to increase the duration of immunity conferred and it is expected that a vaccine comprising inactivated or attenuated Treponema spirohetes will be effective to actively immunize susceptible mammals against PDD.

Furthermore, it is expected that the efficacy of vaccines based on PDD-associated Treponema spp. will b e increased by employing immunogenic fractions derived therefrom by methods which are known to the art. For example, the treponemal outer envelope which surrounds the protoplasmic cylinder of spirochetes can be readily extracted (Klaviter et al., *Acta. Trop.* 36:123 (1979)). This fraction may provide immunogens which impart an equal or greater resistance to PDD infection when employed as the active component of vaccines prepared in accord with the present invention. Recombinant outer surface proteins may also be used as an immunogen.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A biologically pure culture of ungulate Treponema selected from the group consisting of Treponema strain 1-9185MED (ATCC Accession No. 202030) and Treponema strain 2-1498 (ATCC Accession No. 202031).

2. A pharmaceutical composition comprising a pharmaceutically acceptable carrier and an immunogenically effective amount of an ungulate Treponema culture of claim 1.

3. The composition of claim 2, further comprising an antigen from an organism that causes ungulate foot rot selected from the group consisting of *Fusobacterium necrophorum, Porphyromonas levii,* and *Dichelobacter nodosus.*

4. The composition of claim 2, further comprising a bovine respiratory syncytial virus antigen, a bovine Herpes virus antigen, a leptospiral antigen, a bovine diarrhea virus antigen, a bovine parainfluenza virus antigen, a vesicular stomatitis virus antigen, a malignant catarrhal fever virus antigen, a blue tongue virus antigen, a pseudorabies virus antigen, a rabies virus antigen, a rinderpest virus antigen, or a Clostridia species antigen.

5. The composition of claim 1, wherein the ungulate Treponema culture is inactivated.

6. The composition of claim 5, wherein the ungulate Treponema culture is inactivated by freezing, lyophilization, or chemical treatment.

7. The composition of claim 1, wherein the composition is formulated for parenteral administration.

* * * * *

UNITED STATES PATENT AND TRADEMARK OFFICE
CERTIFICATE OF CORRECTION

PATENT NO. : 6,287,575 B1
DATED : September 11, 2001
INVENTOR(S) : Walker et al.

It is certified that error appears in the above-identified patent and that said Letters Patent is hereby corrected as shown below:

Column 42,
Lines 31 and 36, delete "claim 1" and insert -- claim 2 --.

Signed and Sealed this

Twentieth Day of August, 2002

Attest:

Attesting Officer

JAMES E. ROGAN
Director of the United States Patent and Trademark Office